US012662433B2

(12) United States Patent
Paterson

(10) Patent No.: US 12,662,433 B2
(45) Date of Patent: Jun. 23, 2026

(54) PROCESS FOR PRODUCING METHANE

(71) Applicant: BP P.L.C., London (GB)

(72) Inventor: Alexander James Paterson, Yorkshire (GB)

(73) Assignee: BP P.L.C., London (GB)

( * ) Notice: Subject to any disclaimer, the term of this patent is extended or adjusted under 35 U.S.C. 154(b) by 467 days.

(21) Appl. No.: 18/252,690

(22) PCT Filed: Dec. 21, 2021

(86) PCT No.: PCT/IB2021/062138

§ 371 (c)(1),
(2) Date: May 11, 2023

(87) PCT Pub. No.: WO2022/137138

PCT Pub. Date: Jun. 30, 2022

(65) Prior Publication Data

US 2024/0002315 A1 Jan. 4, 2024

(30) Foreign Application Priority Data

Dec. 22, 2020 (EP) .................................... 20216751

(51) Int. Cl.
*C07C 1/12* (2006.01)
*B01J 21/04* (2006.01)
(Continued)

(52) U.S. Cl.
CPC ................. *C07C 1/12* (2013.01); *B01J 21/04* (2013.01); *B01J 21/063* (2013.01); *B01J 21/066* (2013.01);
(Continued)

(58) Field of Classification Search
CPC ... C07C 1/12; C07C 2521/06; C07C 2523/34; C07C 2523/75; C07C 2523/76;
(Continued)

(56) References Cited

U.S. PATENT DOCUMENTS 4,291,126 A 9/1981 Sugier et al.
2002/0173555 A1* 11/2002 Ionkina .................. B01J 23/74 518/715

FOREIGN PATENT DOCUMENTS

CN 102941098 A 2/2013
CN 102949998 A 3/2013
(Continued)

OTHER PUBLICATIONS

Rodemerck et al. "Catalyst Development for CO2 Hydrogenation to Fuels." Chemcatchem., 2013, vol. 5, pp. 1948-1955.
(Continued)

*Primary Examiner* — Jafar F Parsa
(74) *Attorney, Agent, or Firm* — McDonnell Boehnen Hulbert & Berghoff LLP

(57) ABSTRACT

The present disclosure relates generally to processes for the production of methane from hydrogen and carbon dioxide. In particular, the disclosure provides for a process for providing a product composition comprising methane. The process includes contacting a gaseous mixture comprising hydrogen and carbon dioxide with a supported methane synthesis catalyst, the supported methane synthesis catalyst comprising cobalt in the range of 1 wt % to 35 wt % on an elemental basis, to provide the product composition with a methane selectivity of at least 75%.

20 Claims, 3 Drawing Sheets

(51) Int. Cl.

| | |
|---|---|
| ***B01J 21/06*** | (2006.01) |
| ***B01J 23/75*** | (2006.01) |
| ***B01J 23/889*** | (2006.01) |

(52) U.S. Cl.
CPC .......... *B01J 23/75* (2013.01); *B01J 23/8892* (2013.01); *C07C 2521/06* (2013.01); *C07C 2523/34* (2013.01); *C07C 2523/75* (2013.01); *C07C 2523/76* (2013.01)

(58) Field of Classification Search
CPC . C07C 9/04; C07C 2521/04; C07C 2523/889; B01J 21/04; B01J 21/063; B01J 21/066; B01J 23/75; B01J 23/8892
See application file for complete search history.

(56) References Cited

FOREIGN PATENT DOCUMENTS

| | | | |
|---|---|---|---|
| CN | 108264093 | A | 7/2017 |
| CN | 107405607 | A | 11/2017 |
| JP | H08-127545 | A | 5/1996 |
| JP | 2019-188281 | A | 10/2019 |
| JP | 2019-188340 | A | 10/2019 |
| WO | 2004022480 | A2 | 3/2004 |
| WO | 2018054963 | A1 | 3/2018 |
| WO | 2019154885 | A1 | 8/2019 |
| WO | 2020064929 | A1 | 4/2020 |

OTHER PUBLICATIONS

Franken Tanja et al., "Solid Solutions in Reductive Environment—A Case Study on Improved CO2 Hydrogenation to Methane on Cobalt Based Catalysts Derived from Ternary Mixed Metal Oxides by Modified Reducibility", Journal of Catalysis, vol. 382, Jan. 20, 2020, pp. 385-394.

Schubert Miriam et al., "Highly Active Co/Al2O3—Based Catalysts for CO 2 Methanation with Very Low Platinum Promotion Prepared by Double Flame Spray Pyrolysis", Catalysis Science & Technology, vol. 6, No. 2, Jan. 1, 2016, pp. 7449-7460.

Natpakan Srisawad et al., "CO2 hydrogenation over Co/Al2O3 Catalysts Prepared via a Solid-state Reaction of Fine Gibbsite and Cobalt Precursors", Reaction Kinetics, Mechanisms and Catalysis, vol. 107, No. 1, May 27, 2012, pp. 179-188.

International Search Report and Written Opinion for PCT/IB2021/062138, 11 pages, mailed Mar. 11, 2022.

Extended European Search Report for EP 20216751.6, 10 pages, mailed Jun. 14, 2021.

Barrett Elliott et al., "The Determination of Pore Volume and Area Distributions in Porous Substances. I. Computations from Nitrogren Isotherms", J Am Chem. Soc., vol. 73, Jan. 1951, pp. 373-380.

Qi, Jiang "The Methanation of Carbon Dioxide on Support Cobalt Catalyst" Coal Conversion, 2000, vol. 23, issue 4, pp. 87-91, provided with English language abstract.

Yuwen, Zhuo, Chapter 3. Effect of Co loading on the catalytic performance of Co/TiO2 for CO methanation: Preparation, modification, and catalyst methylation of CO2 by Co-based catalysts, Master's Thesis, Tsinghua University, Beijin, China, 2018, pp. 28-41, provided with machine translation.

* cited by examiner

PROCESS FOR PRODUCING METHANE

This application is a national stage application under 35 U.S.C. § 371 of International Application No. PCT/IB2021/062138, filed Dec. 21, 2021, which claims priority to EP application Ser. No. 20/216,751.6, filed Dec. 22, 2020, incorporated by reference herein in their entirety.

BACKGROUND OF THE DISCLOSURE

Field

The present disclosure relates to processes for the production of methane from mixtures of hydrogen and carbon dioxide, especially from renewable sources.

Technical Background

The conversion of synthesis gas into hydrocarbons by the Fischer-Tropsch process has been known for many years. The growing importance of alternative energy sources has resulted in renewed interest in the Fischer-Tropsch (FT) process as it allows a direct and environmentally acceptable route to high-quality fuels and feedstock chemicals through use of bio-derived carbon sources.

FT processes are typically used to produce linear hydrocarbons for use in fuels, as well as oxygenates which can also be useful in fuels and otherwise serve as valuable feedstock chemicals. The hydrocarbon fuel derived from FT processes can be better able to meet increasingly stringent environmental regulations compared to conventional refinery-produced fuels, as FT-derived fuels typically have lower contents of sulfur, nitrogen, and aromatic compounds, which contribute to the emission of potent pollutants such as $SO_2$, $NO_x$, and particulates. Alcohols derived from FT processes often have a higher octane rating than hydrocarbons and thus burn more completely, thereby reducing the environmental impact of such a fuel. Alcohols and other oxygenates obtained may also be used as feedstocks for other processes, such as in the synthesis of lubricants.

A variety of transition metals have been identified to be catalytically active in the conversion of synthesis gas into hydrocarbons and oxygenated derivatives thereof. In particular, cobalt, nickel, and iron have been studied, often in combination with a support material, of which the most common are alumina, silica and carbon.

Typically, Fischer-Tropsch reactions utilize carbon monoxide as the carbon source due to its increased reactivity compared to carbon dioxide. However, utilization of carbon dioxide is of great interest due to its prevalence as a waste gas and low cost. One method to utilize carbon dioxide in a Fischer-Tropsch process is through the so-called "reverse water gas shift reaction," in which carbon dioxide is reacted with hydrogen to produce carbon monoxide and water. The produced carbon monoxide may then be subjected to a Fisher-Tropsch synthesis. However, this conversion must be carried out at exceptionally high temperatures, often in excess of 900° C., and thus is energetically unfavorable.

Accordingly, there remains a need to develop processes to more efficiently utilize carbon dioxide in the production of hydrocarbons.

SUMMARY

The present inventor has found processes to efficiently convert carbon dioxide and hydrogen to methane using a cobalt-based Fischer-Tropsch synthesis catalyst.

Accordingly, one aspect of the disclosure provides for a process for providing a product composition comprising methane, the process comprising:

- contacting a gaseous mixture comprising hydrogen and carbon dioxide with a supported methane synthesis catalyst, the supported methane synthesis catalyst comprising cobalt in the range of 1 wt % to 35 wt %, to provide the product composition with a methane selectivity of at least 75%.

Another aspect of the present disclosure is a method of producing a hydrocarbon composition, the method comprising:

- reforming a reforming feed comprising methane with water and/or oxygen to produce a reforming product stream comprising carbon monoxide and hydrogen, wherein at least a portion of the methane is produced by the processes as otherwise described herein.

Another aspect of the present disclosure is a Fischer-Tropsch process comprising contacting a hydrocarbon synthesis mixture comprising carbon monoxide and hydrogen with a Fischer-Tropsch hydrocarbon synthesis catalyst to produce a hydrocarbon composition with a selectivity for $C_{5+}$ hydrocarbons of at least 50% and/or a selectivity for oxygenates of at least 20%, wherein at least a portion of carbon monoxide and/or hydrogen is produced by the processes as otherwise described herein.

Other aspects of the disclosure will be apparent to those skilled in the art in view of the description that follows.

DETAILED DESCRIPTION

Figure 1:
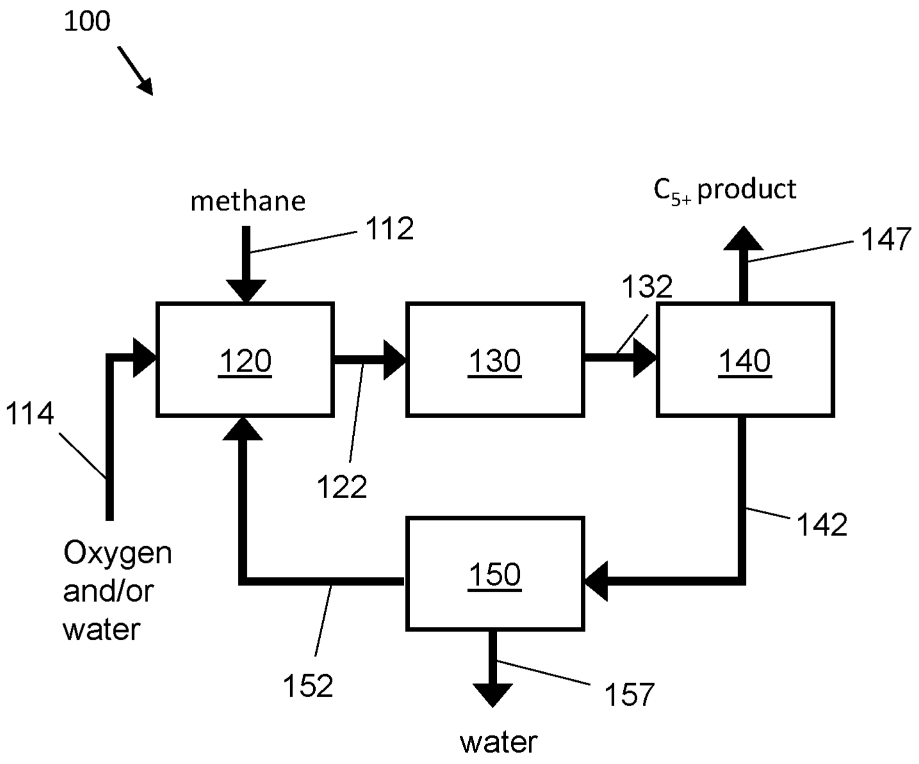
FIG. 1 provides a process schematic according to one embodiment of the disclosure.

The present disclosure is concerned with processes to efficiently produce methane from a mixture of carbon dioxide and hydrogen. Carbon dioxide is an attractive starting material due to its widespread availability and low cost, and especially because it can conveniently be produced from renewable sources, e.g., as a byproduct of fermentation or combustion, or through gasification of biomass. Methods to convert carbon dioxide into hydrocarbons that can be used as fuels and lubricant are especially attractive out of environmental concerns. However, due to its nonpolarity and thermodynamic stability, carbon dioxide is typically less reactive than carbon monoxide, and so it is less preferred for use in Fischer-Tropsch processes. To overcome this challenge, carbon dioxide can be reacted with hydrogen in the reverse water gas shift reaction to produce carbon monoxide and water. However, this extra step is energy intensive, as reverse water gas shift reactors are typically run at temperatures exceeding 900° C., leading to high operating costs and expensive reactor design.

In contrast, the present inventor has determined that methane can be provided from carbon dioxide without relying on the reverse water gas shift reaction. Surprisingly, contact of carbon dioxide and hydrogen with a cobalt-containing Fisher-Tropsch synthesis catalyst and operate at much lower temperatures than those used for a reverse water gas shift reaction. This allows for lower energy consumption and lower capital cost associated operating a reverse water gas shift reactor.

Accordingly, one aspect of the disclosure provides for a process for providing a product composition comprising methane, the process comprising:

contacting a gaseous mixture comprising hydrogen and carbon dioxide with a supported methane synthesis catalyst, the supported methane synthesis catalyst comprising cobalt in the range of 1 wt % to 35 wt %, to provide the product composition with a methane selectivity of at least 75%.

An advantage of the processes of the present disclosure is the ability to produce methane from a gaseous mixture that has low amounts of (or even substantially no) carbon monoxide. In certain embodiments as otherwise described herein, the gaseous mixture comprises no more than 10 wt % carbon monoxide. For example, in particular embodiments, the gaseous mixture comprises no more than 8 wt % (e.g., no more than 5 wt %, or 4 wt %, or 3 wt %, or 2 wt % or 1 wt % carbon monoxide. In certain embodiments, the gaseous mixture comprises no more than 0.5 wt % carbon monoxide (e.g., no more than 0.2 wt %, or 0.1 wt %, 500 ppm, or 100 pm, or is substantially free of carbon monoxide).

The gaseous mixture used as a feed for the production of methane can advantageously comprise more carbon dioxide than carbon monoxide. Notably, carbon monoxide has been found to decrease the effectiveness of the conversion to methane. Thus, in certain embodiments as otherwise described herein, the gaseous has a weight ratio of carbon dioxide to carbon monoxide at least 5:1, e.g., at least 10:1. For example, in certain embodiments, the gaseous mixture has a weight ratio of carbon dioxide to carbon monoxide of at least 15:1, e.g., 20:1, or 50:1, or 100:1, or 200:1, or 500:1. Of course, when substantially no carbon monoxide is present, the ratio can be much higher.

In the processes disclosed herein, carbon dioxide is reacted with hydrogen to produce methane. As such, the gaseous mixture includes both carbon dioxide and hydrogen. The carbon dioxide and hydrogen can be provided to a reactor as a combined stream, or can separately be fed to a reactor to provide the mixture therein. In certain embodiments as otherwise described herein, the molar ratio of hydrogen to carbon dioxide ($H_2$:$CO_2$) in the gaseous mixture is at least 0.5:1, e.g., at least 1:1, at least 1.5:1, at least 2:1, or at least 3:1. In certain embodiments as otherwise described herein, the volume ratio of hydrogen to carbon dioxide in the gaseous mixture is at most 10:1, e.g., at most 7:1, or at most 5:1, at most 4:1. Examples of suitable molar ratios of hydrogen to carbon dioxide in the gaseous mixture include the ranges from 0.5:1 to 10:1, e.g., from 0.5:1 to 7:1; or from 0.5:1 to 5:1; or from 0.5:1 to 4:1; or from 1:1 to 10:1; or from 1:1 to 7:1; or from 1:1 to 5:1; or from 2:1 to 10:1; or from 2:1 to 7:1; or from 2:1 to 5:1; or from 3:1 to 10:1; or from 3:1 to 7:1; or from 3:1 to 5:1. In certain desirable embodiments, the molar ratio of hydrogen to carbon dioxide is in the range of from 1:1 to 4:1, e.g., from 1:1 to 3.5:1 or from 1:1 to 3:1 or from 1.5:1 to 4:1, or from 1.5:1 to 3.5:1, or from 1.5:1 to 3:1, or from 2:1 to 3:1, or from 2:1 to 3.5:1, or from 2:1 to 3:1.

The gaseous reactant stream may also comprise other gaseous components, such as nitrogen, water, methane, carbon monoxide and other saturated and/or unsaturated light hydrocarbons (i.e., $C_4$ and below), each preferably being present at a concentration of less than 30% by volume. In certain embodiments as otherwise described herein, at least 20 vol % of the gaseous mixture is hydrogen and carbon dioxide, e.g., at least 30 vol %, at least 40 vol %, or at least 50 vol %. In certain embodiments as otherwise described herein, at least 50 vol % of the gaseous mixture is hydrogen, carbon dioxide and nitrogen, e.g., at least 60 vol %, at least 70 vol %, at least 80 vol %, or at least 90 vol %. In certain embodiments as otherwise described herein, at least 50 vol % of the gaseous mixture is hydrogen, carbon dioxide, nitrogen water and methane, e.g., at least 60 vol %, at least 70 vol %, at least 80 vol %, or at least 90 vol %.

As described above, the supported methane synthesis catalyst used in the processes of the disclosure comprises in the range of 1 wt % to 35 wt % cobalt on an elemental basis. Notably, many catalysts that are conventionally used in Fischer-Trospch processes are surprisingly suitable for the methane synthesis processes described herein. The person of ordinary skill in the art will, based on the disclosure herein, select a suitable amount of cobalt. For example, in certain embodiments, the supported methane synthesis catalyst comprises cobalt in an amount in the range of 1-30 wt %, or 1-25 wt %, or 1-20 wt %, or 2-35 wt %, or 2-30 wt %, or 2-25 wt %, or 2-20 wt %, or 5-35 wt %, or 5-30 wt %, or 5-25 wt %, or 10-35 wt %, or 10-30 wt %, or 10-25 wt %, on an elemental basis. In certain particular embodiments, the supported methane synthesis catalyst comprises cobalt in an amount in the range of 2-20 wt %, e.g., 2-15 wt %, or 2-10 wt %, or 5-20 wt %, or 5-15 wt %, or 5-10 wt %, or 7-20 wt %, or 7-15 wt %, or 7-12 wt %, or 10-20 wt %, or 10-15 wt %, on an elemental basis.

In certain desirable embodiments as otherwise described herein, the supported methane synthesis catalyst includes at least 0.5 wt % manganese on an elemental basis. In certain embodiments, the supported methane synthesis catalyst comprises no more than 20 wt % manganese on an elemental basis. For example, the supported methane synthesis catalyst may comprise manganese in the range of 0.5 to 20 wt % on an elemental basis, for example, in the range of 0.5-15 wt %, or 0.5-10 wt %, or 0.5-7 wt %, or 0.5-5 wt %, or 1-20 wt %, or 1-15 wt %, or 1-10 wt %, or 1-5 wt %, or 2-20 wt %, or 2-15 wt %, or 2-10 wt %, or 2-5 wt %, or 5-20 wt %, or 5-15 wt %, or 5-12 wt %, or 5-10 wt %, or 7-20 wt %, or 7-15 wt %, or 7-12 wt %, on an elemental basis.

Without being bound by any particular theory, it is believed that the presence of manganese contributes to surface effects on the solid support that influence cobalt oxide crystallite development and dispersivity at the surface. This may derive from the mobility of cobalt-containing precursor compound(s) which are applied to the support material during catalyst preparation, for instance suspended or dissolved in an impregnation solution, whilst in the presence of manganese-containing precursor compound(s). Thus, catalysts especially suitable for use herein can involve cobalt-containing precursor compound(s) and manganese-containing precursor compound(s) being applied to a support material such that they form a mobile admixture at the surface of the support during its preparation.

In certain embodiments as otherwise described herein, the total amount of cobalt and manganese in the synthesis catalyst is no more than 40 wt % on an elemental basis, based on the total weight of the synthesis catalyst. For example, in particular embodiments the total amount of cobalt and manganese in the methane synthesis catalyst is no more than 30 wt %, or no more than 25 wt %, or no more than 22 wt %, or no more than 20 wt %. In certain embodiments, the total amount of cobalt and manganese in the synthesis catalyst is no more than 15 wt %. In certain embodiments as otherwise described herein, the total amount of cobalt and manganese in the methane synthesis catalyst is at least 2 wt % on an elemental basis, based on the total weight of the methane synthesis catalyst. For example, in particular embodiments the total amount of cobalt and manganese in the methane synthesis catalyst is at least 5 wt %, or at least 8 wt %, or at least 10 wt %.

The person of ordinary skill in the art will appreciate that suitable supported methane synthesis catalyst may also possess a wide variety of other transition metals. For example, a variety of promoters, such as one or more of ruthenium, palladium, platinum, rhodium, rhenium, chromium, nickel, iron, molybdenum, tungsten, zirconium, gallium, thorium, lanthanum, cerium, copper and mixtures thereof may be included. Promoter is typically used in a cobalt to promoter atomic ratio of up to 250:1, e.g., up to 125:1, or up to 25:1, or up to 10:1. In certain such embodiments, the one or more promoters are present in the cobalt-containing Methane synthesis catalyst obtained in an amount from 0.1 wt % to 3 wt %, on an elemental basis, based on the total weight of the supported synthesis catalyst. In other embodiments, the cobalt-containing methane synthesis catalyst does not contain any such promoters.

A particular active cobalt surface area has been found to improve catalyst performance. In certain embodiments as otherwise described herein, the supported methane synthesis catalyst has an active cobalt surface area in the range of 2 $m^2/g$ to 15 $m^2/g$ (e.g., 3 to 12 $m^2/g$, or 4 $m^2/g$ to 10 $m^2/g$). Active cobalt surface area is determined through hydrogen chemisorption.

In certain embodiments as otherwise described herein, the supported methane synthesis catalyst has a total surface area in the range of 5 $m^2/g$ to 350 $m^2/g$. The BET surface area, pore volume, pore size distribution and average pore radius are determined from the nitrogen adsorption isotherm determined at 77K using a Micromeritics TRISTAR 3000 static volumetric adsorption analyser, according to application of British Standard methods BS4359:Part 1:1984 'Recommendations for gas adsorption (BET) methods' and BS7591:Part 2:1992, 'Porosity and pore size distribution of materials'—Method of evaluation by gas adsorption. The resulting data may be reduced using the BET method (over the pressure range 0.05-0.20 P/Po) and the Barrett, Joyner & Halenda (BJH) method (for pore diameters of 20-1000 Angstroms) to yield the surface area and pore size distribution respectively. Suitable references for the above data reduction methods are Brunauer, S, Emmett, P H, & Teller, E, J. Amer. Chem. Soc. 60, 309, (1938) and Barrett, E P, Joyner, LG & Halenda P P, J. Am Chem. Soc., 1951 73 373-380.

The supported methane synthesis catalyst comprises a support material. The support material serves to bind the catalyst particles and may also influence the catalytic activity. In certain embodiments as otherwise described herein, the support material includes at least one of alumina, zirconia, titania, silica, zinc oxide, ceria, or combinations thereof. In particular embodiments, the support material comprises one of alumina, zirconia, zinc oxide, ceria, silica and titania, for example the support material is one of alumina, zirconia, zinc oxide, ceria, silica and titania. In other particular embodiments, the support material comprises one of alumina, zirconia, zinc oxide, ceria, and titania, for example the support material is one of alumina, zirconia, zinc oxide, ceria, and titania. In other particular embodiments, the support material comprises one of zirconia, zinc oxide, ceria, and titania, for example the support material is one of zirconia, zinc oxide, ceria, and titania. In yet other particular embodiments, the support material comprises titania, for example the support material is titania.

The supported methane synthesis catalyst used in accordance with the present disclosure may be prepared by any suitable method that is able to provide the required manganese to cobalt weight ratio and the required concentration of manganese on the supported. Preferably, the supported methane synthesis catalyst used in accordance with the present disclosure is prepared by a process in which the cobalt and the manganese are impregnated on to the support material.

A suitable impregnation method, for example, comprises impregnating a support material with cobalt-containing compound, which is thermally decomposable to the oxide form, and a manganese-containing compound. Impregnation of the support material with the cobalt-containing compound and the manganese-containing compound may be achieved by any suitable method of which the skilled person is aware, for instance by vacuum impregnation, incipient wetness or immersion in excess liquid.

The incipient wetness technique is so-called because it requires that the volume of impregnating solution be predetermined so as to provide the minimum volume of solution necessary to just wet the entire surface of the support, with no excess liquid. The excess solution technique as the name implies, requires an excess of the impregnating solution, the solvent being thereafter removed, usually by evaporation.

The support material may be in the form of a powder, granulate, shaped particle, such as a preformed sphere or microsphere, or extrudate. Reference herein to a powder or granulate of a support material is understood to refer to free flowing particles of a support material or particles of support material that have undergone granulation and/or sieving to be a particular shape (e.g. spherical) and size range. Reference herein to an "extrudate" is intended to mean a support material that has undergone an extrusion step and therefore may be shaped. In the context of the present disclosure, the powder or granulate is in a form which is suitable for impregnation with a solution of cobalt-containing compound and manganese-containing compound, and subsequent extrusion or forming into other shaped particles.

It will be understood that the support material may be in any form provided it is suitable for use as a support for a Methane synthesis catalyst and also preferably where the support material has not been previously impregnated with sources of metal (i.e., other than cobalt and/or manganese) that may have a deleterious effect on the performance of the active catalyst and may interfere with the benefits of the processes of the disclosure. Thus, whilst support material that has been previously loaded with cobalt and/or manganese metal, or precursors thereof, may be used in accordance with the disclosure, other pre-treatments providing sources of other metals are preferably to be avoided. Preferred support materials are substantially free of extraneous components which might adversely affect the catalytic activity of the system. Thus, preferred support materials are at least 95% w/w pure, more preferably at least 98% w/w pure and most preferably at least 99% w/w pure. Impurities preferably amount to less than 1% w/w, more preferably less than 0.50% w/w and most preferably less than 0.25% w/w. The pore volume of the support is preferably more than 0.150 ml/g and preferably more than 0.30 ml/g. The average pore radius (prior to impregnation) of the support material is 10 to 500 A, preferably 15 to 100 Angstroms, more preferably 20 to 80 A and most preferably 25 to 60 A. The BET surface area is suitably from 2 to 1000 $m^2g$, preferably from 10 to 600 $m^2/g$, more preferably from 15 to 300 $m^2/g$, and most preferably 30 to 150 $m^2/g$.

When in the form of a powder, the median particle size diameter (d50) is preferably less than 50 pm, more preferably less than 25 μm. When the support material is in the form of a granulate, the median particle size diameter (d50) is preferably from 300 to 600 μm. Particle size diameter (d50) may suitably be determined by means of a particle size analyser (e.g. Microtrac S3500 Particle size analyser).

It is known to be beneficial to perform Fischer-Tropsch catalysis with a shaped particle, such as an extrudate, particularly in the case of fixed catalyst bed reactor systems; such catalysts are likewise useful in the methane synthesis processes described herein. For instance, it is known that, for a given shape of catalyst particles, a reduction in the size of the catalyst particles in a fixed bed gives rise to a corresponding increase in pressure drop through the bed. Thus, the relatively large shaped particles cause less of a pressure drop through the catalyst bed in the reactor compared to the corresponding powdered or granulated supported catalyst. Shaped particles, such as extrudates, also generally have greater strength and experience less attrition, which is of particular value in fixed bed arrangements where bulk crush strength must be very high.

Reference herein to "impregnation" or "impregnating" is intended to refer to contact of the support material with a solution, or solutions, of, for example, a cobalt-containing compound and a manganese-containing compound, before drying in order to achieve precipitation of the cobalt-containing compound and the manganese-containing compound. Impregnation with a fully dissolved solution, or solutions, of a cobalt-containing compound and a manganese-containing compound ensures good dispersion of the cobalt-containing compound and the manganese-containing compound on the support material and is thus preferred. This is in contrast, for instance, to the use of partially dissolved cobalt-containing compound and/or a partially dissolved manganese-containing compound in 'solid solutions' or suspensions, where the level of dispersion of the cobalt-containing compound and manganese-containing compound across the surface, and in the pores, of the support material can fluctuate depending on the nature of the precipitation on the support material. Furthermore, use of a fully dissolved solution, or solutions, of cobalt-containing compound and manganese-containing compound also has less of an impact upon the resulting morphology and bulk crush strength of an extrudate formed thereafter compared with solid solutions. Nevertheless, benefits of the processes of the present disclosure can also be realised in the case where a solid solution, or solutions, of a partially undissolved cobalt-containing compound and/or manganese-containing compound is used.

Where a powder or granulate of a support material is contacted with a solution, or solutions, of cobalt-containing compound and manganese-containing compound, the amount of solution used preferably corresponds to an amount of liquid which is suitable for achieving a mixture which is of a suitable consistency for further processing, for example for shaping by extrusion. In that case, complete removal of the solvent of the impregnating solution may be effected after formation of the shaped particle, such as an extrudate.

Suitable cobalt-containing compounds are those which are thermally decomposable to an oxide of cobalt following calcination and which are preferably completely soluble in the impregnating solution. Preferred cobalt-containing compounds are the nitrate, acetate or acetylacetonate of cobalt, most preferably the nitrate of cobalt, for example cobalt nitrate hexahydrate. It is preferred to avoid the use of the halides because these have been found to be detrimental.

Suitable manganese-containing compounds are those which are thermally decomposable following calcination and which are preferably completely soluble in the impregnating solution. Preferred manganese-containing compounds are the nitrate, acetate or acetylacetonate of manganese, most preferably the acetate of manganese.

The solvent of the impregnating solution(s) may be either an aqueous solvent or a non-aqueous, organic solvent. Suitable non-aqueous organic solvents include, for example, alcohols (e.g. methanol, ethanol and/or propanol), ketones (e.g. acetone), liquid paraffinic hydrocarbons and ethers. Alternatively, aqueous organic solvents, for example an aqueous alcoholic solvent, may be employed. Preferably, the solvent of the impregnating solution(s) is an aqueous solvent.

In preferred embodiments, the impregnation of the support material with a cobalt-containing compound and a manganese-containing compound occurs in a single step, without any intermediate drying or calcination steps to separate the loading of the different components. As the skilled person will appreciate, the cobalt-containing compound and manganese-containing compound may be applied to the support material successively or simultaneously in separate impregnation solutions or suspensions, or preferably an impregnation solution or suspension comprising both the cobalt-containing compound and the manganese-containing compound is used.

The concentration of the cobalt-containing compound and the manganese-containing compound, in the impregnating solution(s) is not particularly limited, although preferably the cobalt-containing compound and the manganese-containing compound are fully dissolved, as discussed hereinbefore. When a powder or granulate of support material is impregnated and immediately followed by an extrusion step, the amount of the impregnating solution(s) is preferably suitable for forming an extrudable paste.

A suitable concentration of cobalt-containing compound and/or manganese-containing compound is, for example, 0.1 to 15 moles/litre.

It will be appreciated that where the support material is in powder or granulate form, once impregnated with a cobalt containing compound and a manganese-containing compound, the impregnated support material may be extruded or formed into shaped particles at any suitable stage before or after drying and calcining.

Impregnation of the support material is usually followed by drying of the impregnating solution in order to effect precipitation of the cobalt-containing compound and the manganese-containing compound on to the support material and preferably also to remove bound solvent of the impregnating solution (e.g. water). Drying therefore does not, for instance, lead to full decomposition of the cobalt-containing compound or otherwise lead to a change in oxidation state of the cobalt-containing compound. As will be appreciated, in embodiments where an extrusion is performed, complete drying and removal of solvent (e.g. bound solvent) of the impregnating solution may occur after forming of a shaped particle, for example by extrusion. Drying is suitably conducted at temperatures from 50° C. to 150° C., preferably 75° C. to 125° C. Suitable drying times are, for example, from 5 minutes to 72 hours. Drying may suitably be conducted in a drying oven or in a box furnace, for example, under the flow of an inert gas at elevated temperature.

Where a shaped particle, such as an extrudate, is impregnated, it will be appreciated that the support may be contacted with the impregnating solution by any suitable means including, for instance, vacuum impregnation, incipient wetness or immersion in excess liquid, as mentioned hereinbefore. Where a powder or granulate of support material is impregnated, the powder or granulate may be admixed with the impregnating solution by any suitable means of which the skilled person is aware, such as by adding the powder or granulate to a container of the impregnating solution and stirring.

Where a step of forming a shaped particle, such as an extrusion step, immediately follows impregnation of a powder or granulate, the mixture of powder or granulate and impregnating solution may be further processed if it is not already in a form which is suitable for forming a shaped particle, for instance by extrusion. For instance, the mixture may be mulled to reduce the presence of larger particles that may not be readily extruded or otherwise formed into a shaped particle, or the presence of which would otherwise compromise the physical properties of the resulting shaped particle, for example an extrudate. Mulling typically involves forming a paste which is suitable for shaping, such as by extrusion. Any suitable mulling or kneading apparatus of which the skilled person is aware may be used for mulling in the context of the present disclosure. For example, a pestle and mortar may suitably be used in some applications or a Simpson muller may suitably be employed. Mulling is typically undertaken for a period of from 3 to 90 minutes, preferably for a period of 5 minutes to 30 minutes. Mulling may suitably be undertaken over a range of temperatures, including ambient temperatures. A preferred temperature range for mulling is from 15° C. to 50° C. Mulling may suitably be undertaken at ambient pressures. As stated hereinbefore, it will be appreciated that complete removal of bound solvent from the impregnation solution may be conducted to effect complete precipitation after forming of the shaped particle, such as by extrusion.

In embodiments where a calcination step is performed on an impregnated powder or granulate, thereby completely removing solvent of the impregnation solution, the calcined powder or granulate may also be further processed in order to form a mixture which is suitable for forming into shaped particles, for example by extruding. For instance, an extrudable paste may be formed by combining the calcined powder or granulate with a suitable solvent, for example a solvent used for impregnation, preferably an aqueous solvent, and mulled as described above.

Preparation of the supported methane synthesis catalyst may involve a calcination step. As will be understood, calcination is required for converting the cobalt-containing compound which has been impregnated on the support material into an oxide of cobalt. Thus, calcination leads to thermal decomposition of the cobalt-containing compound, and not merely removal of bound solvent of an impregnating solution, as for instance in the case of drying.

Calcination may be performed by any method known to those of skill in the art, for instance in a fluidized bed or rotary kiln at a temperature of at least 250° C., preferably from 275° C. to 500° C. In some embodiments, calcination may be conducted as part of an integrated process where calcination and reductive activation of the synthesis catalyst to yield a reduced Fisher-Tropsch synthesis catalyst are performed in the same reactor. In a particularly preferred embodiment, the supported methane synthesis catalyst used in the process of the disclosure is obtained or obtainable from a process comprising the steps of:

(a) impregnating a support material with: a cobalt-containing compound and a manganese-containing compound in a single impregnation step to form an impregnated support material; and
(b) drying and calcining the impregnated support material to form the supported methane synthesis catalyst.

A particular advantage of this embodiment is the expediency with which a support material may be modified and converted into a supported methane synthesis catalyst using only a single impregnation step followed by a drying and calcination step. Thus, in preferred embodiments, the support material used in connection with the processes of the disclosure has undergone no prior modification, for instance by the addition of promoters, dispersion aids, strength aids and/or binders, or precursors thereof, before impregnation in step (a) of the process.

The person of ordinary skill in the art will perform the processes described herein using any desirable reaction systems. For example, a wide variety of reactors can be used, e.g., a fixed bed reactor, a slurry bed reactor, or a fluid bed reactor. So-called CANs reactor systems can be advantageously used.

Advantageously, the processes of the present disclosure may be conducted at relatively low temperatures compared to conventional methods to transform carbon dioxide into hydrocarbons. In certain embodiments as otherwise described herein, the contacting of the gaseous mixture comprising hydrogen and carbon dioxide with the supported methane synthesis catalyst is performed at a temperature in the range of 150° C. to 325° C. (e.g., in the range of 150° C. to 300° C., or 150° C. to 275° C., or 150° C. to 270° C., or 150° C. to 260° C., or 150° C. to 250° C., or 175° C. to 325° C., or 175° C. to 275° C., or 175° C. to 270° C., or 175° C. to 260° C., or 175° C. to 250° C., or 200° C. to 325° C., or 200° C. to 275° C., or 200° C. to 270° C., or 200° C. to 260° C., or 200° C. to 250° C.). In certain embodiments as otherwise described herein, the contacting of the gaseous mixture comprising hydrogen and carbon dioxide with the supported methane synthesis catalyst is performed at a pressure in the range from 10 to 100 bar (from 1 to 10 MPa). For example, in certain embodiments, the contacting is performed at a pressure in the range of 20 barg to 80 barg, e.g., in the range of 20 barg to 60 barg, or 20 barg to 50 barg, or 20 barg to 40 barg.

The supported methane synthesis catalyst may conveniently be converted into a reduced supported methane synthesis catalyst by reductive activation by any known means of which the skilled person is aware which is capable of converting cobalt oxide to the active cobalt metal. Further, the present inventors have found that activation through reduction of the catalyst at relatively low temperatures gives equal or improved catalyst performance compared to high temperature reduction. This surprising result allows for improved catalyst yields as well as energy savings. Thus, in one embodiment, the process of the disclosure further comprises a preceding step of activating the methane synthesis catalyst by a method comprising reducing the catalyst with a reducing gas at a temperature of no more than 350° C. to form a supported methane synthesis catalyst synthesis catalyst comprising cobalt(0). In particular embodiments, the reducing gas comprises hydrogen gas. The step of forming a reduced synthesis catalyst may be carried out batch wise or continuously in a fixed bed, fluidised bed or slurry phase reactor, or in-situ in the same reactor as will be subsequently used for the methane synthesis reaction. Reduction is suitably performed at a temperature of from 150° C. to 350° C., e.g., from 150° C. to 325° C., or from 200° C. to 325° C.

Activation conditions, including the lowered temperature, can be designed to limit the amount of cobalt that is converted to cobalt metal. For example, the catalyst may impregnated with the catalyst in an oxidized, cationic form. Subsequent calcination may be used to convert the metal to an oxide. Then, catalyst reduction may be used to transform at least a portion of the metal to the metallic, zero-valent form (e.g., cobalt(0)). Accordingly, in certain embodiments as otherwise described herein, at least 70% (e.g., more than 80%, or more than 90%) of the cobalt of the supported methane synthesis catalyst is cobalt(0), on an atomic basis following reduction.

Advantageously, the supported methane synthesis catalyst may be passivated in order to prevent deactivation upon exposure to air. Passivation may be desirable in order to store, transport, load and/or unload the catalyst. Once installed in the reactor, the catalyst may be re-activated. Accordingly, in certain embodiments as otherwise described herein, the process further comprises passivating the supported methane synthesis catalyst by contacting the supported methane synthesis catalyst with a passivation agent (e.g., a passivating agent comprising oxygen) to form a passivated methane synthesis catalyst; and re-activating the supported methane synthesis catalyst by contacting the supported methane synthesis catalyst with a reducing agent at temperature of no more than 350° C. In particular embodiments, the passivation agent is oxygen, optionally admixed with one or more of water, nitrogen, and carbon dioxide. In certain embodiments as otherwise described herein, the process further comprises, prior to the re-activating step, transporting the passivated methane synthesis catalyst and charging a reactor bed with the passivated methane synthesis catalyst.

As will be appreciated, the gaseous reactant mixture supplied to the methane synthesis reaction may also be suitable for reducing the supported methane synthesis catalyst to form a reduced supported methane synthesis catalyst in situ, without requiring any preceding or distinct reductive activation step.

In particular embodiments, the hydrogen utilized in the processes described herein comprises hydrogen from renewable or carbon-neutral sources. Green hydrogen is defined as hydrogen gas produced without any reliance on fossil fuels, either for the feedstock or for energy input. Accordingly, in certain embodiments as otherwise described herein, the hydrogen comprises green hydrogen. For example, at least 50% (e.g., at least 75%, or at least 90% or at least 95%) of the hydrogen is green hydrogen.

One potential source of green hydrogen is through water electrolysis. In particular embodiments, the hydrogen may be formed through the electrolysis of water. Numerous methods of electrolysis are known in the art. For example, electrolysis may be performed on pure water to produce hydrogen gas and oxygen gas, or on other solutions, such as saline solution, to produce hydrogen gas and another product (e.g., chlorine gas). In particular embodiments, the hydrogen is formed through the electrolysis of a saline solution. Water electrolysis is described further in U.S. Pat. Nos. 4,312,720, 4,021,323, and 4,094,751, each of which is incorporated by reference in their entirety.

To qualify as green hydrogen, the electrical power used for the water electrolysis must be from a renewable source, that is, a source that does not depend on fossil fuel combustion. Example sources of renewable power include solar power through photovoltaic capture or solar thermal technology, wind power, geothermal energy capture, hydroelectric energy, or other renewable sources. Appropriate renewable energy sources are known to those of skill in the art, and may optionally be selected through certification by an appropriate agency.

Blue hydrogen is defined as hydrogen gas produced with some reliance on fossil fuels, but in a process that is overall carbon neutral (i.e., does not result in any net introduction of carbon dioxide into the atmosphere). In certain embodiments as otherwise described herein, the hydrogen utilized in the processes as otherwise described herein comprises blue hydrogen. An example of blue hydrogen is hydrogen gas produced from fossil fuel-derived hydrocarbons such as methane gas, wherein the resulting carbon product is captured or otherwise utilized. For example, steam reforming of methane may be conducted to produce three moles of hydrogen gas and one mole of carbon monoxide for each mole of methane. Methane steam reforming is highly endothermic, requiring significant energy input. Of course, the energy required to perform these processes must be sources from renewable sources, or sources with adequate carbon capture technology. Accordingly, in certain embodiments as otherwise described herein, at least a portion of the hydrogen (e.g., at least 50%, at least 75%, at least 90% or at least 95%) is formed through the steam reforming of methane. Steam reforming of methane to produce hydrogen is discussed in International Patent Application Publication no. 2004/022480, which is herein incorporated by reference in its entirety.

Advantageously, the carbon dioxide utilized in the processes described herein may be carbon dioxide collected from the atmosphere or that would otherwise have been released into the atmosphere, e.g., from a combustion or other industrial process. The carbon dioxide may be captured, where it is collected or absorbed after release from an industrial process, or absorbed directly from the atmosphere. Methods of carbon capture are known to those of skill in the art. In certain embodiments, the carbon dioxide comprises captured carbon dioxide, e.g., at least 50%, at least 75%, at least 90% or at least 95% of the carbon dioxide is captured carbon dioxide.

Alternatively, biomass is an attractive source of renewable carbon dioxide for use in the processes described herein. One source of biomass is agricultural products in the form of dedicated energy crops such as switchgrass, miscanthus, bamboo, sorghum, tall fescue, kochia, wheatgrass, poplar, willow, silver maple, eastern cottonwood, green ash, black walnut, sweetgum, and sycamore. Another biomass source is agricultural waste or agricultural crop residue. Conventional agricultural activities, including the production of food, feed, fiber, and forest products, generate large amounts of waste plant material. Examples of such materials include corn stover, wheat straw, oat straw, barley straw, soghum stubble, and rice straw. A third biomass source is through forestry residues left after timber operations. Biomass may also be in the form of municipal waste, which includes commercial and residential garbage, including yard trimmings, paper and paperboard, plastics, rubber, leather, textiles, and food waste. Accordingly, in certain embodiments as otherwise described herein, the crude syngas is derived from biomass, for example, agricultural biomass or municipal waste biomass. Additional sources of agricultural biomass will be apparent to one of skill in the art as dictated by local availability, economics, and process compatibility.

To generate carbon dioxide from a carbon-containing material, such as biomass, the material much be subjected to gasification. Gasification involved heating the material under controlled conditions to generate gaseous streams of carbon monoxide, hydrogen, and carbon dioxide. Controlled amounts of other reactants, such as oxygen and/or steam, may be used to modify the process. Gasification conditions are tuned in accordance with the carbon-containing material being gasified in order to efficiently produce gaseous products. In certain embodiments as otherwise described herein, the carbon dioxide comprises carbon dioxide from the gasification of biomass. The biomass may be any source as described above, or from multiple sources may be combined. In certain embodiments, the carbon dioxide comprises carbon dioxide from gasification of biomass, e.g., at least 50%, at least 75%, at least 90% or at least 95% of the carbon dioxide is from gasification of biomass.

As used herein, "selectivity" for a given component is measured as the molar fraction of a particular reactant that is reacted in the process (i.e., not including any unreacted portion of that particular reactant) and is converted to that product. For example, in the reaction of carbon dioxide and hydrogen to provide product components including methane, "selectivity" for a given component is defined as the molar fraction of carbon dioxide that is reacted in the process and is converted to the product of interest, not including any unreacted carbon dioxide. Selectivity for a Fischer-Tropsch process is calculated with respect to CO and $CO_2$ in the feed.

Advantageously, the processes described herein can produce a product composition with a high selectivity for methane. In certain embodiments as otherwise described herein, the selectivity for methane is at least 80% (e.g., at least 85%, or at least 90%, or at least 95%). It may be desirable to limit the selectivity for $C_{5+}$ hydrocarbons. In certain embodiments as otherwise described herein, the carbon dioxide is reacted with a $C_{5+}$ selectivity of no more than 10%, e.g., no more than 8%, or no more than 7%, or no more than 5%, or no more than 4%, or no more than 3%. In certain embodiments as otherwise described herein, the carbon dioxide is reacted with a $C_{2+}$ selectivity of no more than 25%, e.g., no more than 20%, or no more than 15%, or no more than 10%, or no more than 5%. It may also be desirable to limit the selectivity for oxygenates. Oxygenates are oxygen-containing molecules, such as alcohols, ethers, esters, carboxylic acids, and the like (but not including carbon dioxide or carbon monoxide). In certain embodiments as otherwise described herein, the carbon dioxide is reacted with an oxygenate selectivity of no more than 10%, e.g., no more than 8%, or no more than 7%, or no more than 5%, or no more than 4%, or no more than 3%.

The processes of the present disclosure advantageously efficiently convert carbon dioxide to methane. High conversions of carbon dioxide is a major challenge in the art, as carbon dioxide can often be relatively inert except for in extreme temperature and/or pressure regimes. The present inventors have developed methods that allow high conversion of carbon dioxide in relatively mild conditions. Accordingly, in certain embodiments as otherwise described herein, the product composition is provided with a carbon dioxide conversion of at least 25%, e.g., at least 30% or at least 35%, or at least 40%, or at least 45%, or at least 50%. As used herein, "conversion" of carbon dioxide is the molar fraction of carbon dioxide that is converted to other species in the reaction. Of course, the person of ordinary skill in the art will appreciate that any unreacted carbon dioxide can be separated and recycled for use as part of the carbon dioxide feed.

A method of utilizing carbon dioxide is the reverse water gas shift reaction, where carbon dioxide and hydrogen are converted to carbon monoxide and water:

$$CO_2 + H_2 \rightleftharpoons CO_2 + H_2O$$

However, the reverse water gas shift reaction it typically performed at in extreme conditions, with reaction temperatures in excess of 900° C. Thus, the reaction is costly from an energy standpoint, and specialized equipment must be used. Further, the process consumes hydrogen which is often expensive in process economics. An advantage of the processes of the present disclosure is the ability to convert carbon dioxide to usable hydrocarbons, including methane, without using the reverse water gas shift reaction. Accordingly, in certain embodiments as otherwise described herein, the process does not include a reverse water gas shift reaction. It is possible that a small proportion of carbon dioxide are converted to carbon monoxide by the reverse water-gas shift reaction as a reaction side product during normal operation of the processes described herein. Accordingly, the absence of a reverse water-gas shift reaction is understood to mean that there is not a distinct reaction zone dedicated to the reverse water-gas shift reaction. Desirably, the processes described herein have a selectivity for carbon monoxide of less than 1%, e.g., less than 1000 ppm or even less than 100 ppm.

Methane is a valuable feedstock for a variety of chemical processes. And when made using carbon dioxide from renewable sources using the processes described herein (e.g., capture from atmosphere or other chemical processes, or biomass conversion), it can be advantageously be considered as a carrier for renewable carbon. Similarly, when made using green hydrogen and/or blue hydrogen as described herein (e.g., electrolysis of water or steam reforming), the methane can be considered as a carrier of hydrogen from such sources.

Methane reforming is commonly utilized to convert methane to carbon monoxide and hydrogen, for example, for use in Fischer-Tropsch synthesis. Accordingly, another aspect of the disclosure is a method of producing a synthesis gas composition comprising carbon monoxide and hydrogen, the method comprising: reforming a reforming feed comprising methane with water and/or oxygen to produce a reforming product stream comprising carbon monoxide and hydrogen, wherein at least a portion of the methane is produced by the processes as otherwise described herein. The reforming of methane can be performed in a reforming zone separate from the zone in which the conversion to methane is performed. In fact, the methane can be produced at a different site, then transported to the site at which the reforming is performed. Several reforming techniques are known in the art. In certain embodiments, the reforming is at least one of steam reforming, autothermal reforming, gas heated reforming, and partial oxidation reforming. For example, the reforming may be a steam reforming. In a steam reforming process, methane is contacted with steam at elevated temperatures and pressures. For example, the steam reforming, in certain embodiments, may be carried out with a reaction temperature of at least 1000° C. and a pressure in the range of 10 barg to 45 barg. In certain embodiments as otherwise described herein, the reforming is steam reforming using a steam reforming catalyst comprising at least one or nickel, rhodium, copper, and cobalt, alternatively or in combination with noble metals such as platinum, palladium rhodium, ruthenium, and iridium. The catalyst may be supported by a composition comprising magnesia, magnesium aluminate, alumina, silica, zirconia, or a combination thereof. For example, in certain embodiments the steam reforming catalyst is a single metal (e.g., nickel) supported on a refractory carrier. The catalyst may also comprise a promoter. Examples of suitable promoters include alkali metals (e.g., potassium). Methods of methane reforming are described, for example, in U.S. Pat. No. 6,749,829, incorporated herein in its entirety.

The reforming product stream comprises carbon monoxide and hydrogen. However, this reforming product stream may not have the ideal $H_2$:CO ratio for an efficient Fischer-Tropsch hydrocarbon synthesis reaction. Further, the person of ordinary skill in the art will appreciate that the $H_2$:CO ratio may be advantageously tuned in response to particular process requirement (e.g., to adjust product selectivity or operation efficiency). Accordingly, in certain embodiments as otherwise described herein, the process further comprises subjecting the reforming product stream to a shift reaction (e.g., a water gas shift reaction) in increase the ratio of hydrogen to carbon monoxide. In other embodiments, the process further comprises subjecting the reforming product stream to a reverse water gas shift reaction in decrease the ratio of hydrogen to carbon monoxide.

And as noted above, such mixtures of carbon monoxide and hydrogen are useful in the synthesis of higher hydrocarbons via the Fischer-Tropsch process. Accordingly, another aspect of the disclosure is a Fischer-Tropsch process comprising contacting a hydrocarbon synthesis mixture comprising carbon monoxide and hydrogen with a Fischer-Tropsch hydrocarbon synthesis catalyst to produce a hydrocarbon composition comprising $C_{5+}$ hydrocarbons and/or oxygenates with a selectivity for $C_{5+}$ hydrocarbons of at least 50% and/or a selectivity for oxygenates of at least 20%, wherein at least a portion of the carbon monoxide and/or hydrogen is produced by a process as otherwise described herein, e.g., by the reforming process described above. In certain embodiments as otherwise described herein, the Fischer-Tropsch hydrocarbon synthesis catalyst used in this Fischer-Tropsch process may have a composition similar to that of the methane synthesis catalyst as otherwise generically described herein. For example, the Fischer-Tropsch hydrocarbon synthesis catalyst may be the same as the methane synthesis catalyst utilized for the production of methane. The person of skill in the art may choose appropriate Fischer-Tropsch hydrocarbon synthesis parameters in light of the present disclosure and in view of the existing state of the art. Suitable techniques for hydrocarbon synthesis, especially with regard to the synthesis of $C_{5+}$ hydrocarbons and/or oxygenates, are described in International Patent Application Publication No. 2019/154885, hereby incorporated by reference herein in its entirety.

It may be desirable to limit the methane production in the hydrocarbon synthesis, as longer chain hydrocarbons are often more valuable. In certain embodiments as otherwise described herein, the contacting of the hydrocarbon synthesis feed to provide the hydrocarbon product stream has a selectivity for methane of no more than 25% (e.g., no more than 20%, or no more than 15%, or no more than 10%). In certain embodiments as otherwise described herein, the contacting of the hydrocarbon synthesis feed to provide the hydrocarbon product stream has a selectivity for $C_{5+}$ hydrocarbons of at least 50% (e.g., at least 60%, or at least 70%, or at least 80%, or at least 90%). In some embodiments, the hydrocarbon synthesis conditions may be adjusted as known in the art to favor the production of oxygenates, see, e.g., WO 2019/154885. In certain embodiments as otherwise described herein, the hydrocarbon product stream comprises oxygenates, and the contacting of the hydrocarbon synthesis feed to provide the hydrocarbon product stream has an oxygenate selectivity of at least 20% (e.g., at least 30%, or at least 40%, or at least 50%).

Subsequent to the formation of the hydrocarbon product stream, it may be desirable to purify the product stream. Accordingly, in certain embodiments as otherwise described herein, the hydrocarbon product stream is separated to produce a $C_{5+}$ hydrocarbon product stream and/or an oxygenate product stream, and a $C_{1-4}$ hydrocarbon product stream. In particular embodiments, the process further comprises recycling the $C_{1-4}$ product stream to provide at least a portion of the reforming feed.

One embodiment of a process of the disclosure is shown in schematic view in FIG. 1. In process 100, a reforming feed 112 is reformed, for example in a reforming zone 120 (such as a reforming reactor). Water and/or oxygen are also provided to the reforming zone 120 via stream 114. The reforming provides a reforming product stream 122 that includes carbon monoxide and hydrogen. This hydrogen and carbon monoxide-containing stream (after optional water-gas shift or reverse water-gas shift, not shown), is contacted with a Fischer-Tropsch hydrocarbon synthesis catalyst, here, in a Fischer-Tropsch reaction zone 130 (e.g., a reactor with a bed of the catalyst therein). The contacting produces a produce a hydrocarbon product stream 132 comprising $C_{5+}$ hydrocarbons and/or oxygenates. As described above, this product stream 132 can be separated, here, in separator 140 to provide a $C_{5+}$ product stream 147 and a stream 142 comprising light hydrocarbons and water, which can be separated from one another in separator 150 to provide a light hydrocarbon stream 152 and a water stream 157. The light hydrocarbon stream 152 can be recycled, e.g., to the reforming reaction zone 120.

As described above, methane can be provided from a number of sources. Accordingly, in the embodiment of FIG. 1, methane can be provided by a pipeline from another site. Such pipeline methane can be provided from conventional sources, or alternatively from renewable sources. For example, such pipeline methane can be provided using the methane synthesis techniques as described herein. In such embodiments, the methane can advantageously act as a carrier for renewable hydrogen and/or carbon.

Figure 2:
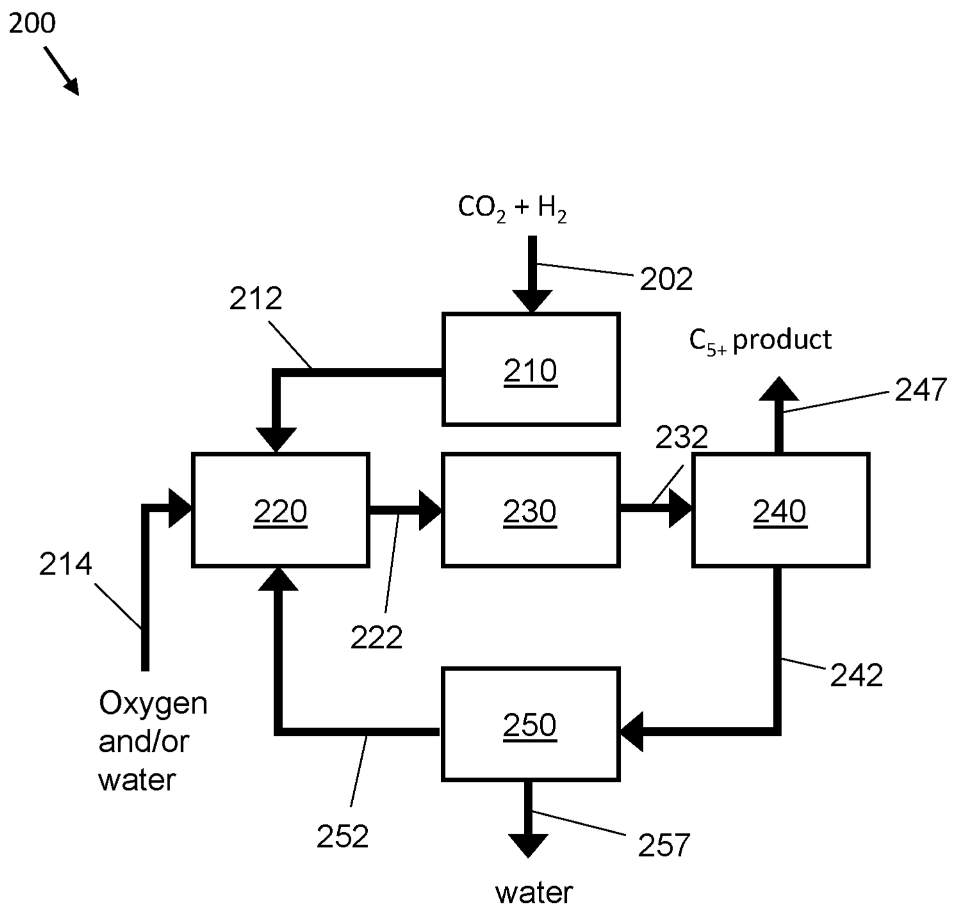
FIG. 2 provides a process schematic according to one embodiment of the disclosure.

Another embodiment of the disclosure is shown in FIG. 2. Here, in an integrated process 200, a carbon dioxide and hydrogen-containing feed 202 is contacted with a methane synthesis catalyst, for example, in methane synthesis zone 210 (e.g., reactor with a bed of the catalyst therein) to provide a methane product stream 212. Methane of this methane product stream 212 is reformed, for example in a reforming zone 220 (such as a reforming reactor). Water and/or oxygen are also provided to the reforming zone 220 via stream 214. The reforming provides a reforming product stream 222 that includes carbon monoxide and hydrogen. This hydrogen and carbon monoxide-containing stream (after optional water-gas shift or reverse water-gas shift, not shown), is contacted with a Fischer-Tropsch hydrocarbon synthesis catalyst, here, in a Fischer-Tropsch reaction zone 230 (e.g., a reactor with a bed of the catalyst therein). The contacting produces a produce a hydrocarbon product stream 232 comprising $C_{5+}$ hydrocarbons and/or oxygenates. As described above, this product stream 232 can be separated, here, in separator 240 to provide a $C_5$ product stream 247 and a stream 242 comprising light hydrocarbons and water, which can be separated from one another in separator 250 to provide a light hydrocarbon stream 252 and a water stream 257. The light hydrocarbon stream 252 can be recycled, e.g., to the reforming reaction zone 220.

The processes of the disclosure will now be further described by reference to the following Examples which are illustrative only. In the Examples, $CO_2$ conversion is defined as moles of $CO_2$ used/moles of $CO_2$ fed×100 and carbon selectivity as moles of $CO_2$ attributed to a particular product/moles of $CO_2$ converted×100. Unless otherwise stated, temperatures referred to in the Examples are applied temperatures and not catalyst/bed temperatures. Unless otherwise stated, pressures referred to in the Examples are absolute pressures.

EXAMPLES

The Examples that follow are illustrative of specific embodiments of the methods of the disclosure, and various uses thereof. They are set forth for explanatory purposes only, and are not to be taken as limiting the scope of the disclosure.

Example 1: Conversion of Hydrogen and Carbon Dioxide to Methane

Several catalysts of varying composition, each analogous to conventional Fischer-Tropsch catalysts, were prepared and loaded into a 16 channel reactor with common feed, temperature and pressure between catalyst channels, with online analysis for $C_1$-$C_8$. The catalysts were activated by heating from 25° C. to 150° C. at 2° C./min, and then heating at 1° C./min from 150° C. to 300° C. under 100% $H_2$ in the 16 channel reactorat atmospheric pressure and a 5000 $hr^1$ gas hourly space velocity. The $CO_2$ conversion reaction was performed at 30 barg and the GHSV stated in the table with a $H_2$:$CO_2$ ratio of 2:1, 1:1, 3:1, 1.8:1, 4:1, and 2:1 (see Tables 1, 2, 3, 4, 6, and 7 respectively) with 51% $N_2$. No carbon monoxide was present in the feed.

TABLE 1

$H_2$:$CO_2$ ratio of 2:1

| Catalyst Loading Description | Applied Temperature ° C. | GHSV $hr^{-1}$ | $CO_2$ Conversion % | $CH_4$ Selectivity % | $C_2$-$C_4$ Selectivity % | $C_{5+}$ Selectivity % |
|---|---|---|---|---|---|---|
| 10% Co/$TiO_2$ | 215 | 6811 | 20.7 | 96.4 | 4.2 | 0.9 |
| 10% Co/1% Mn/$TiO_2$ | 215 | 8153 | 19.4 | 97.9 | 2.5 | 1.2 |
| 10% Co/2% Mn/$TiO_2$ | 215 | 8212 | 19.3 | 99.7 | 1.8 | 0.0 |
| 10% Co/3% Mn/$TiO_2$ | 215 | 3431 | 29.3 | 97.4 | 2.6 | 0.6 |
| 10% Co/5% Mn/$TiO_2$ | 215 | 2908 | 36.2 | 94.2 | 4.6 | 1.6 |
| 10% Co/5% Mn/ZnO | 245 | 3639 | 44.0 | 93.3 | 6.7 | 0.6 |
| 10% Co/10% Mn/ZnO | 245 | 3018 | 43.6 | 93.0 | 7.1 | 0.4 |
| 10% Co/5% Mn/$ZrO_2$ | 245 | 8816 | 43.0 | 95.0 | 6.0 | 0.2 |
| 10% Co/5% Mn/$Al_2O_3$ | 245 | 17589 | 32.5 | 95.7 | 4.6 | 0.2 |
| 10% Co/1% Mn/$CeO_2$ | 245 | 1610 | 44.9 | 92.5 | 8.2 | 0.5 |
| 10% Co/5% Mn/$CeO_2$ | 245 | 3013 | 46.1 | 95.0 | 6.1 | 0.2 |
| 10% Co/10% Mn/$CeO_2$ | 245 | 2799 | 46.2 | 93.6 | 6.6 | 0.6 |

TABLE 2

| H$_2$:CO$_2$ ratio of 1:1 | | | | | | |
|---|---|---|---|---|---|---|
| Catalyst Loading Description | Applied Temperature ° C. | GHSV $hr^{-1}$ | $CO_2$ Conversion % | $CH_4$ Selectivity % | $C_2$-$C_4$ Selectivity % | $C_{5+}$ Selectivity % |
| 10% Co/$TiO_2$ | 215 | 6896.6 | 11.8 | 96.4 | 5.3 | 0.0 |
| 10% Co/1% Mn/$TiO_2$ | 215 | 8273.9 | 10.6 | 94.4 | 3.1 | 2.2 |
| 10% Co/2% Mn/$TiO_2$ | 215 | 8351.2 | 10.3 | 96.3 | 2.6 | 1.1 |
| 10% Co/3% Mn/$TiO_2$ | 215 | 3488.8 | 16.0 | 93.5 | 3.9 | 2.2 |
| 10% Co/5% Mn/$TiO_2$ | 215 | 2961.7 | 19.9 | 90.3 | 6.4 | 3.0 |
| 10% Co/5% Mn/ZnO | 245 | 3452.5 | 21.3 | 87.2 | 8.8 | 3.4 |
| 10% Co/10% Mn/ZnO | 245 | 2863.6 | 21.2 | 87.1 | 9.1 | 3.5 |
| 10% Co/5% Mn/$ZrO_2$ | 245 | 8384.1 | 20.6 | 88.6 | 8.3 | 3.2 |
| 10% Co/5% Mn/$Al_2O_3$ | 245 | 16675.0 | 16.0 | 91.3 | 6.2 | 2.5 |
| 10% Co/1% Mn/$CeO_2$ | 245 | 1521.9 | 21.8 | 84.3 | 11.6 | 3.6 |
| 10% Co/5% Mn/$CeO_2$ | 245 | 2860.5 | 22.4 | 88.4 | 8.7 | 2.6 |
| 10% Co/10% Mn/$CeO_2$ | 245 | 2656.5 | 22.3 | 88.0 | 9.2 | 3.2 |

TABLE 3

| H$_2$:CO$_2$ ratio of 3:1 | | | | | | |
|---|---|---|---|---|---|---|
| Catalyst Loading Description | Applied Temperature ° C. | GHSV $hr^{-1}$ | $CO_2$ Conversion % | $CH_4$ Selectivity % | $C_2$-$C_4$ Selectivity % | $C_{5+}$ Selectivity % |
| 10% Co/$TiO_2$ | 215 | 6829.2 | 24.48 | 94.3 | 3.7 | 2.3 |
| 10% Co/1% Mn/$TiO_2$ | 215 | 8526.4 | 19.02 | 96.3 | 1.9 | 3.2 |
| 10% Co/2% Mn/$TiO_2$ | 215 | 8536.7 | 20.23 | 97.1 | 1.3 | 2.0 |
| 10% Co/3% Mn/$TiO_2$ | 215 | 3515.9 | 29.41 | 95.6 | 2.2 | 2.7 |
| 10% Co/5% Mn/$TiO_2$ | 215 | 3059.9 | 37.27 | 96.2 | 2.6 | 2.4 |
| 10% Co/5% Mn/ZnO | 245 | 3543.2 | 46.20 | 92.8 | 4.0 | 4.0 |
| 10% Co/10% Mn/ZnO | 245 | 2956.5 | 46.05 | 91.5 | 3.9 | 4.7 |
| 10% Co/5% Mn/$ZrO_2$ | 245 | 8505.6 | 43.30 | 92.7 | 4.7 | 3.2 |
| 10% Co/5% Mn/$Al_2O_3$ | 245 | 17105.0 | 32.00 | 91.0 | 5.0 | 4.7 |
| 10% Co/1% Mn/$CeO_2$ | 245 | 1525.8 | 55.36 | 90.4 | 6.0 | 3.7 |
| 10% Co/5% Mn/$CeO_2$ | 245 | 2973.6 | 51.67 | 90.2 | 6.0 | 4.0 |
| 10% Co/10% Mn/$CeO_2$ | 245 | 2640.9 | 52.98 | 90.1 | 5.8 | 4.3 |

TABLE 4

| H$_2$:CO$_2$ ratio of 1.8:1 | | | | | | |
|---|---|---|---|---|---|---|
| Catalyst Loading Description | Applied Temperature ° C. | GHSV $hr^{-1}$ | $CO_2$ Conversion % | $CH_4$ Selectivity % | $C_2$-$C_4$ Selectivity % | $C_{5+}$ Selectivity % |
| 10% Co/$TiO_2$ | 215 | 6828.1 | 18.96 | 95.9 | 3.9 | 1.1 |
| 10% Co/1% Mn/$TiO_2$ | 215 | 8546.7 | 16.44 | 96.4 | 2.3 | 0.9 |
| 10% Co/2% Mn/$TiO_2$ | 215 | 8487.3 | 18.52 | 97.9 | 1.8 | 0.7 |
| 10% Co/3% Mn/$TiO_2$ | 215 | 3470.5 | 26.76 | 96.5 | 2.5 | 1.7 |
| 10% Co/5% Mn/$TiO_2$ | 215 | 3012.8 | 33.80 | 93.7 | 3.6 | 2.6 |
| 10% Co/5% Mn/ZnO | 245 | 3444.7 | 39.2 | 90.4 | 7.1 | 2.6 |
| 10% Co/10% Mn/ZnO | 245 | 2886.5 | 39.7 | 91.3 | 6.4 | 1.7 |
| 10% Co/5% Mn/$ZrO_2$ | 245 | 8350.6 | 41.1 | 91.5 | 6.4 | 2.0 |
| 10% Co/5% Mn/$Al_2O_3$ | 245 | 16712.0 | 34.8 | 92.6 | 4.5 | 2.5 |
| 10% Co/1% Mn/$CeO_2$ | 245 | 1523.4 | 34.8 | 85.3 | 11.8 | 3.0 |
| 10% Co/5% Mn/$CeO_2$ | 245 | 2883.7 | 42.1 | 89.8 | 7.4 | 2.9 |
| 10% Co/10% Mn/$CeO_2$ | 245 | 2584.7 | 42.4 | 90.6 | 6.8 | 2.2 |

TABLE 5

| Summary of Test Conditions for the results presented in Tables 1-4 | | | | | | | | | |
|---|---|---|---|---|---|---|---|---|---|
| Catalyst Description | Applied Temp. ° C. | $CO_2$ Conv. @1:1 % | $CH_4$ Sel. % | $CO_2$ Conv. @1.8:1 % | $CH_4$ Sel. % | $CO_2$ Conv. @2:1 % | $CH_4$ Sel. % | $CO_2$ Conv. @3:1 % | $CH_4$ Sel. % |
| 10% Co/$TiO_2$ | 215 | 11.8 | 96.4 | 18.96 | 95.9 | 20.2 | 96.4 | 24.48 | 94.3 |
| 10% Co/1% Mn/$TiO_2$ | 215 | 10.6 | 94.4 | 16.44 | 96.4 | 18.9 | 97.9 | 19.02 | 96.3 |
| 10% Co/2% Mn/$TiO_2$ | 215 | 10.3 | 96.3 | 18.52 | 97.9 | 18.8 | 99.7 | 20.23 | 97.1 |

TABLE 5-continued

| Summary of Test Conditions for the results presented in Tables 1-4 | | | | | | | | | |
|---|---|---|---|---|---|---|---|---|---|
| Catalyst Description | Applied Temp. ° C. | $CO_2$ Conv. @1:1 % | $CH_4$ Sel. % | $CO_2$ Conv. @1.8:1 % | $CH_4$ Sel. % | $CO_2$ Conv. @2:1 % | $CH_4$ Sel. % | $CO_2$ Conv. @3:1 % | $CH_4$ Sel. % |
| 10% Co/3% Mn/$TiO_2$ | 215 | 16.0 | 93.5 | 26.76 | 96.5 | 28.8 | 97.4 | 29.41 | 95.6 |
| 10% Co/5% Mn/$TiO_2$ | 215 | 19.9 | 90.3 | 33.80 | 93.7 | 35.8 | 94.2 | 37.27 | 96.2 |
| 10% Co/5% Mn/ZnO | 245 | 21.3 | 87.2 | 39.2 | 90.4 | 42.8 | 93.3 | 46.20 | 92.8 |
| 10% Co/10% Mn/ZnO | 245 | 21.1 | 87.1 | 39.7 | 91.3 | 42.5 | 93.0 | 46.05 | 91.5 |
| 10% Co/5% Mn/$ZrO_2$ | 245 | 20.6 | 88.6 | 41.1 | 91.5 | 41.8 | 95.0 | 43.30 | 92.7 |
| 10% Co/5% Mn/$Al_2O_3$ | 245 | 16.0 | 91.3 | 34.8 | 92.6 | 31.0 | 95.7 | 32.00 | 91.0 |
| 10% Co/1% Mn/$CeO_2$ | 245 | 21.8 | 84.3 | 34.8 | 34.8 | 85.3 | 43.8 | 92.5 | 90.4 |
| 10% Co/5% Mn/$CeO_2$ | 245 | 22.4 | 88.4 | 42.1 | 42.1 | 89.8 | 45.0 | 95.0 | 90.2 |
| 10% Co/10% Mn/$CeO_2$ | 245 | 22.3 | 88.0 | 88.0 | 42.4 | 90.6 | 45.0 | 93.6 | 90.1 |

Figure 3:
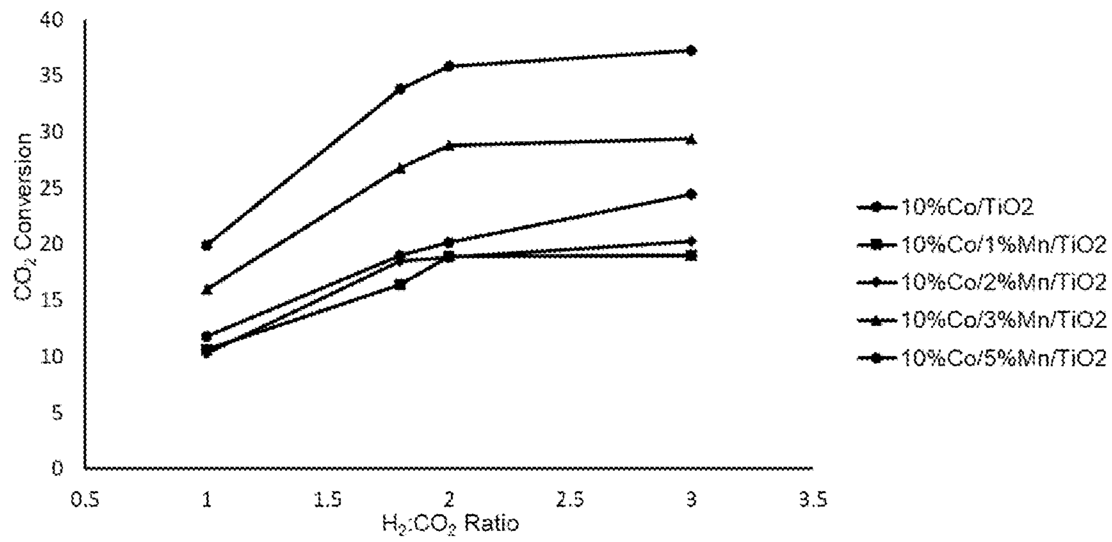
FIG. 3 is a graph showing $CO_2$ conversion as a function of $H_2$:$CO_2$ ratio according to an example embodiment.

As shown in Tables 1-5 and in the summary FIG. 3, the present inventors have surprisingly found conditions that allow for the efficient conversion of hydrogen and carbon dioxide to methane. Importantly, the observed carbon dioxide conversion are advantageously high, as carbon dioxide typically suffers from poor reactivity. This result is especially surprising given the mild reaction temperatures in the range of 215 to 245° C. Further, the processes exhibit high selectivity, with certain parameters yielding methane selectivity of about 95%. This extremely high selectivity allows for efficient processing of the product stream with minimal required purification. Additionally, this activity would not be expected for typical Co/Mn catalysts, because they are typically used in the Fischer-Tropsch synthesis of much larger molecular weight materials.

TABLE 6

| $H_2$:$CO_2$ ratio of 4:1 | | | | |
|---|---|---|---|---|
| Catalyst Loading Description | Applied Temperature ° C. | GHSV $hr^{-1}$ | $CO_2$ Conversion % | $CH_4$ Selectivity % |
| 10% Co/$TiO_2$ | 230 | 3238.8 | 46.5 | 92.1 |
| 10% Co/1% Mn/$TiO_2$ | 230 | 7536.6 | 47.2 | 96.7 |
| 10% Co/2% Mn/$TiO_2$ | 230 | 9181.5 | 40.4 | 97.3 |
| 10% Co/3% Mn/$TiO_2$ | 230 | 3796.9 | 50.6 | 95.6 |
| 10% Co/5% Mn/$TiO_2$ | 230 | 3304.0 | 57.3 | 95.4 |

TABLE 7

| $H_2$:$CO_2$ ratio of 2:1 | | | | |
|---|---|---|---|---|
| Catalyst Loading Description | Applied Temperature ° C. | GHSV $hr^{-1}$ | $CO_2$ Conversion % | $CH_4$ Selectivity % |
| 10% Co/$TiO_2$ | 250 | 4329.5 | 19.4 | 93.3 |
| 10% Co/1% Mn/$TiO_2$ | 250 | 10215.7 | 19.4 | 97.7 |
| 10% Co/2% Mn/$TiO_2$ | 250 | 12325.8 | 14.7 | 100 |
| 10% Co/3% Mn/$TiO_2$ | 250 | 5133.7 | 18.4 | 99.3 |
| 10% Co/5% Mn/$TiO_2$ | 250 | 4457.9 | 21.9 | 94.1 |

As shown in Tables 6 and 7, the high methane selectivity for titania-supported catalysts is maintained at increased temperatures.

Example 2: Steam Reforming of Methane to Produce Carbon Monoxide and Hydrogen

Subsequent to the formation of methane as demonstrated in Example 1, the methane is subjected to purification to remove $C_{2+}$ hydrocarbons and also remove undesirable contaminants. The methane is then transferred to a steam reformer with an outlet temperature of 1065° C. and pressure of 32 bara. Within the steam reformer, the methane is contacted with a combination of oxygen and steam to produce a reformer product stream comprising carbon monoxide and hydrogen.

Example 3: Hydrocarbon Synthesis with Steam Reforming Product Stream

As described in Example 2, the methane produced in Example 1 may be directed to a steam reformer to produce a reformer product stream that includes carbon monoxide and hydrogen. This product stream may be subjected to scrubbing or product separation to purify the carbon monoxide and hydrogen mixture. Other processes may be used to adjust the hydrogen to carbon monoxide ratio. Subsequently, the hydrogen and carbon monoxide are introduced into a Fischer-Tropsch hydrocarbon synthesis reactor. The Fischer-Tropsch hydrocarbon synthesis reactor operates in the range of 200-300° C. and 10-50 bara. The catalyst provided may have the same composition, or generally the same composition, as those utilized in Example 1, or may have a different composition. This process produces a Fischer-Tropsch hydrocarbon composition with high selectivity of $C_{5+}$ hydrocarbon and/or $C_1$-$C_{24}$ oxygenates.

Example 4: Use of Green Hydrogen and Captured Carbon Dioxide

Processes similar to those of Examples 1-3 can be conducted using only green hydrogen, such as hydrogen generated from water electrolysis powered by solar and/or wind. Similarly, carbon dioxide in such processes can be provided from a carbon capture process, such as carbon capture from power generation or industrial chemical synthesis or manufacturing. Optionally, any power required to operate the processes of Examples 1-3 can be sourced from renewable power sources. Overall, this results can result in renewable, carbon neutral or even carbon negative processes to generate valuable hydrocarbons.

Various exemplary embodiments of the disclosure include, but are not limited to the enumerated embodiments listed below, which can be combined in any number and in any combination that is not technically or logically inconsistent.

Embodiment 1. A process for providing a product composition comprising methane, the process comprising:

contacting a gaseous mixture comprising hydrogen and carbon dioxide with a supported methane synthesis catalyst, the supported methane synthesis catalyst comprising cobalt in the range of 1 wt % to 35 wt % on an elemental basis, to provide the product composition with a methane selectivity of at least 75%.

Embodiment 2. The process of Embodiment 1, wherein the gaseous mixture comprises no more than 10 wt % carbon monoxide (e.g., no more than 5 wt %, or 3 wt %, or 2 wt %, or 1 wt % carbon monoxide).

Embodiment 3. The process of Embodiment 1 or Embodiment 2, wherein the gaseous mixture comprises no more than 0.5 wt % carbon monoxide (e.g., no more than 0.2 wt %, or 0.1 wt %, 500 ppm, or 100 pm, or is substantially free of carbon monoxide).

Embodiment 4. The process of any of Embodiments 1-3, wherein the gaseous mixture has a weight ratio of carbon dioxide to carbon monoxide of at least 10:1 (e.g., at least 15:1, or 20:1, or 50:1, or 100:1).

Embodiment 5. The process of any of Embodiments 1-4, wherein hydrogen and the carbon dioxide are present in a molar ratio in the range of from 0.5:1 to 10:1, e.g., from 0.5:1 to 7:1; or from 0.5:1 to 5:1; or from 0.5:1 to 4:1; or from 1:1 to 10:1; or from 1:1 to 7:1; or from 1:1 to 5:1; or from 2:1 to 10:1; or from 2:1 to 7:1; or from 2:1 to 5:1; or from 3:1 to 10:1; or from 3:1 to 7:1; or from 3:1 to 5:1.

Embodiment 6. The process of any of Embodiments 1-4, wherein hydrogen and the carbon dioxide are present in a molar ratio in the range of from 1:1 to 4:1, e.g., from 1:1 to 3.5:1 or from 1:1 to 3:1 or from 1.5:1 to 4:1, or from 1.5:1 to 3.5:1, or from 1.5:1 to 3:1, or from 2:1 to 3:1, or from 2:1 to 3.5:1, or from 2:1 to 3:1.

Embodiment 7. The process of any of Embodiments 1-6, wherein at least 20 vol % of the gaseous mixture is hydrogen and carbon dioxide, e.g., at least 30 vol %, at least 40 vol %, or at least 50 vol %.

Embodiment 8. The process of any of Embodiments 1-7, wherein at least 50 vol % of the gaseous mixture is hydrogen, carbon dioxide and nitrogen, e.g., at least 60 vol %, at least 70 vol %, at least 80 vol %, or at least 90 vol %.

Embodiment 9. The process of any of Embodiments 1-8, wherein at least 50 vol % of the gaseous mixture is hydrogen, carbon dioxide, nitrogen water and methane, e.g., at least 60 vol %, at least 70 vol %, at least 80 vol %, or at least 90 vol %.

Embodiment 10. The process of any of Embodiments 1-9, wherein the supported methane synthesis catalyst comprises cobalt in in an amount in the range of 1-30 wt %, or 1-25 wt %, or 1-20 wt %, or 2-35 wt %, or 2-30 wt %, or 2-25 wt %, or 2-20 wt %, or 5-35 wt %, or 5-30 wt %, or 5-25 wt %, or 10-35 wt %, or 10-30 wt %, or 10-25 wt % on an elemental basis.

Embodiment 11. The process of any of Embodiments 1-9, wherein the supported methane synthesis catalyst comprises cobalt in an amount in the range of 2-20 wt %, e.g., 2-15 wt %, or 2-10 wt %, or 5-20 wt %, or 5-15 wt %, or 5-10 wt %, or 7-20 wt %, or 7-15 wt %, or 7-12 wt %, or 10-20 wt %, or 10-15 wt %, on an elemental basis.

Embodiment 12. The process of any of Embodiments 1-11, wherein the supported methane synthesis catalyst further comprises manganese, wherein the manganese is present in the range of 0.5-15 wt %, or 0.5-10 wt %, or 0.5-7 wt %, or 0.5-5 wt %, or 1-20 wt %, or 1-15 wt %, or 1-10 wt %, or 1-5 wt %, or 2-20 wt %, or 2-15 wt %, or 2-10 wt %, or 2-5 wt %, or 5-20 wt %, or 5-15 wt %, or 5-12 wt %, or 5-10 wt %, or 7-20 wt %, or 7-15 wt %, or 7-12 wt %, on an elemental basis.

Embodiment 13. The process of any of Embodiments 1-12, wherein the supported methane synthesis catalyst has an active cobalt surface area in the range of 2 $m^2/g$ to 15 $m^2/g$.

Embodiment 14. The process of any of Embodiments 1-13, wherein the supported methane synthesis catalyst has a total surface area in the range of 5 $m^2/g$ to 350 $m^2/g$.

Embodiment 15. The process of any of Embodiments 1-14, wherein the supported methane synthesis catalyst comprises a support material comprising at least one of alumina, zirconia, titania, silica, zinc oxide, ceria, or combinations thereof.

Embodiment 16. The process of any of Embodiments 1-15, wherein the contacting is performed at a temperature in the range of 150° C. to 325° C. (e.g., in the range of 150° C. to 300° C., or 150° C. to 275° C., or 150° C. to 250° C., or 175° C. to 325° C., or 175° C. to 275° C., or 175° C. to 250° C., or 200° C. to 325° C., or 200° C. to 275° C., or 200° C. to 250° C.).

Embodiment 17. The process of any of Embodiments 1-16, wherein the contacting is performed at a pressure in the range of 10 barg to 100 barg, e.g., in the range of 20 barg to 80 barg, or 20 barg to 60 barg, or 20 barg to 50 barg, or 20 barg to 40 barg.

Embodiment 18. The process of any of Embodiments 1-17, wherein the selectivity for methane is at least 80% (e.g., at least 85%, or at least 90%, or at least 95%).

Embodiment 19. The process of any of Embodiments 1-18, wherein the carbon dioxide is reacted with a $C_{5+}$ selectivity of no more than 10%, e.g., no more than 8%, or no more than 7%, or no more than 5%, or no more than 4%, or no more than 3%.

Embodiment 20. The process of any of Embodiments 1-19, wherein the carbon dioxide is reacted with a $C_{2+}$ selectivity of no more than 25%, e.g., no more than 20%, or no more than 15%, or no more than 10%, or no more than 5%.

Embodiment 21. The process of any of Embodiments 1-20, wherein the product composition is provided with a carbon dioxide conversion of at least 5%, e.g., at least 10%, or at least 15%, or at least 20%.

Embodiment 22. The process of any of Embodiments 1-21, wherein the carbon dioxide is reacted with a carbon dioxide conversion of at least 25%, e.g., at least 30%, or at least 35%, or at least 40%.

Embodiment 23. The process of any of Embodiments 1-22, wherein the supported methane synthesis catalyst is activated by a method comprising reducing the catalyst with a reducing gas at a temperature of no more than 350° C. to form a supported methane synthesis catalyst comprising cobalt(0).

Embodiment 24. The process of any of Embodiments 1-23, wherein no more than 95% of the cobalt of the methane synthesis catalyst is cobalt(0).

Embodiment 25. The process of any of Embodiment 1-24, further comprising:

passivating the supported methane synthesis catalyst by contacting the supported methane synthesis catalyst with a passivation agent (e.g., a passivating agent comprising oxygen) to form a passivated methane synthesis catalyst; and re-activating the supported methane synthesis catalyst by contacting the supported methane synthesis catalyst with a reducing agent at temperature of no more than 350° C.

Embodiment 25. The process of Embodiment 24, further comprising, prior to the re-activating step, transporting the passivated methane synthesis catalyst and charging a reactor bed with the passivated methane synthesis catalyst.

Embodiment 26. The process of any of Embodiments 1-25, wherein the hydrogen comprises green hydrogen (e.g., hydrogen generated through electrolysis, wherein the electrolysis is powered, at least in part, by renewable energy).

Embodiment 27. The process of any of Embodiments 1-26, wherein the carbon dioxide comprises captured carbon dioxide or carbon dioxide from biomass gasification.

Embodiment 28. The process of any of Embodiments 1-28, wherein the process does not include a reverse water gas shift reaction.

Embodiment 29. A method of producing a synthesis gas composition comprising carbon monoxide and hydrogen, the method comprising:

reforming a reforming feed comprising methane with water and/or oxygen to produce a reforming product stream comprising carbon monoxide and hydrogen, wherein at least a portion of the methane is produced by the process of any of Embodiments 1-28.

Embodiment 30. The process of Embodiment 29, wherein the reforming comprises at least one of steam reforming, autothermal reforming, gas heated reforming, and partial oxidation reforming.

Embodiment 31. The process of Embodiment 29, wherein the reforming is steam reforming using steam reforming catalyst comprising at least one of nickel, rhodium, copper, and cobalt.

Embodiment 32. The process of any of Embodiments 29-31, wherein the reforming zone is performed at a reaction temperature of at least 1000° C., and a pressure in the range of 10 barg to 45 barg.

Embodiment 33. A Fischer-Tropsch process comprising contacting a hydrocarbon synthesis mixture comprising carbon monoxide and hydrogen with a Fischer-Tropsch hydrocarbon synthesis catalyst to produce a hydrocarbon composition with a selectivity for $C_{5+}$ hydrocarbons of at least 50% and/or a selectivity for oxygenates of at least 20%, wherein at least a portion of carbon monoxide and/or hydrogen is produced by a process according to any of Embodiments 29-32.

Embodiment 34. The Fischer-Trospch process according to Embodiment 33, wherein the Fischer-Tropsch hydrocarbon synthesis catalyst is provided in accordance with the description of the methane synthesis catalyst in any above embodiment.

Embodiment 35. A catalyst composition for the conversion of carbon dioxide and hydrogen to methane, the catalyst composition being as described herein, and especially with respect to any of the above embodiments.

Embodiment 36. The catalyst composition according to Embodiment 35, wherein the conversion of carbon dioxide and hydrogen to methane is as described herein, especially with respect to any of the above embodiments.

The particulars shown herein are by way of example and for purposes of illustrative discussion of certain embodiments of the present disclosure only and are presented in the cause of providing what is believed to be the most useful and readily understood description of the principles and conceptual aspects of various embodiments of the disclosure. In this regard, no attempt is made to show details associated with the methods of the disclosure in more detail than is necessary for the fundamental understanding of the methods described herein, the description taken with the examples making apparent to those skilled in the art how the several forms of the methods of the disclosure may be embodied in practice. Thus, before the disclosed processes and devices are described, it is to be understood that the aspects described herein are not limited to specific embodiments, apparatus, or configurations, and as such can, of course, vary. It is also to be understood that the terminology used herein is for the purpose of describing particular aspects only and, unless specifically defined herein, is not intended to be limiting.

The terms "a," "an," "the" and similar referents used in the context of describing the methods of the disclosure (especially in the context of the following embodiments and claims) are to be construed to cover both the singular and the plural, unless otherwise indicated herein or clearly contradicted by context.

All methods described herein can be performed in any suitable order of steps unless otherwise indicated herein or otherwise clearly contradicted by context. The use of any and all examples, or exemplary language (e.g., "such as") provided herein is intended merely to better illuminate the methods of the disclosure and does not pose a limitation on the scope of the disclosure. No language in the specification should be construed as indicating any non-claimed element essential to the practice of the methods of the disclosure.

Unless the context clearly requires otherwise, throughout the description and the claims, the words 'comprise', 'comprising', and the like are to be construed in an inclusive sense as opposed to an exclusive or exhaustive sense; that is to say, in the sense of "including, but not limited to". Words using the singular or plural number also include the plural and singular number, respectively. Additionally, the words "herein," "above," and "below" and words of similar import, when used in this application, shall refer to this application as a whole and not to any particular portions of the application.

As will be understood by one of ordinary skill in the art, each embodiment disclosed herein can comprise, consist essentially of or consist of its particular stated element, step, ingredient or component. As used herein, the transition term "comprise" or "comprises" means includes, but is not limited to, and allows for the inclusion of unspecified elements, steps, ingredients, or components, even in major amounts. The transitional phrase "consisting of" excludes any element, step, ingredient or component not specified. The transition phrase "consisting essentially of" limits the scope of the embodiment to the specified elements, steps, ingredients or components and to those that do not materially affect the embodiment.

All percentages, ratios and proportions herein are by weight, unless otherwise specified.

Notwithstanding that the numerical ranges and parameters setting forth the broad scope of the disclosure are approximations, the numerical values set forth in the specific examples are reported as precisely as possible. Any numerical value, however, inherently contains certain errors necessarily resulting from the standard deviation found in their respective testing measurements.

Groupings of alternative elements or embodiments of the disclosure are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

The phrase "at least a portion" as used herein is used to signify that, at least, a fractional amount is required, up to the entire possible amount.

In closing, it is to be understood that the various embodiments herein are illustrative of the methods of the disclosures. Other modifications that may be employed are within the scope of the disclosure. Thus, by way of example, but not of limitation, alternative configurations of the methods may be utilized in accordance with the teachings herein. Accordingly, the methods of the present disclosure are not limited to that precisely as shown and described.

What is claimed is:

1. A process for providing a product composition comprising methane, the process comprising:

contacting a gaseous mixture comprising hydrogen and carbon dioxide with a supported methane synthesis catalyst, the supported methane synthesis catalyst comprising cobalt in the range of 5 wt % to 20 wt % on an elemental basis, and manganese in the range of 0.5 wt % to 15 wt %, on an elemental basis, to provide the product composition with a methane selectivity of at least 75%.

2. The process of claim 1, wherein the gaseous mixture comprises no more than 5 wt % carbon monoxide.

3. The process of claim 1, wherein hydrogen and the carbon dioxide are present in a molar ratio in the range of from 1:1 to 4:1.

4. The process of claim 1, wherein at least 50 vol % of the gaseous mixture is hydrogen, carbon dioxide and nitrogen.

5. The process of claim 1, wherein the supported methane synthesis catalyst comprises cobalt in an amount in the range of 7-20 wt %, on an elemental basis.

6. The process of claim 1, wherein the supported methane synthesis catalyst comprises manganese, wherein the manganese is present in the range of 0.5-10 wt %, on an elemental basis.

7. The process of claim 1, wherein the supported methane synthesis catalyst comprises a support material comprising at least one of alumina, zirconia, titania, silica, zinc oxide, ceria, or combinations thereof.

8. The process of claim 1, wherein the contacting is performed at a temperature in the range of 150° C. to 325° C.

9. The process of claim 1, wherein the selectivity for methane is at least 80%.

10. The process of claim 1, wherein the carbon dioxide is reacted with a $C_{5+}$selectivity of no more than 10%.

11. The process of claim 1, wherein the product composition is provided with a carbon dioxide conversion of at least 5%.

12. The process of claim 1, wherein the hydrogen comprises green hydrogen, and/or wherein the carbon dioxide comprises captured carbon dioxide or carbon dioxide from biomass gasification.

13. A method of producing a synthesis gas composition comprising carbon monoxide and hydrogen, the method comprising:

performing the process of claim 1 to provide methane, and reforming a reforming feed comprising at least a portion of the methane with water and/or oxygen to produce a reforming product stream comprising carbon monoxide and hydrogen.

14. A Fischer-Tropsch process comprising performing the process of claim 13 to provide carbon monoxide and hydrogen; and contacting a hydrocarbon synthesis mixture comprising at least a portion of the carbon monoxide and at least a portion of the hydrogen with a Fischer-Tropsch hydrocarbon synthesis catalyst to produce a hydrocarbon composition with a selectivity for $C_{5+}$hydrocarbons of at least 50% and/or a selectivity for oxygenates of at least 20%.

15. The process of claim 14, wherein the supported methane synthesis catalyst comprises a support material comprising at least one of zirconia, titania, silica, zinc oxide, ceria, or combinations thereof.

16. The process of claim 15, wherein the supported methane synthesis catalyst is free of alumina.

17. The process of claim 14, wherein the supported methane synthesis catalyst is supported on a titania support material, a zirconia support material, a zinc oxide support material, or a ceria support material.

18. The process of claim 17, wherein the supported methane synthesis catalyst is free of alumina.

19. The process of claim 14, wherein the supported methane synthesis catalyst is supported on a zirconia support material, a zinc oxide support material, or a ceria support material.

20. The process of claim 14, wherein the supported methane synthesis catalyst is supported on a titania support material.

* * * * *